US00PP08820P

United States Patent [19]

Henny

[11] Patent Number: Plant 8,820

[45] Date of Patent: Jul. 5, 1994

[54] ANTHURIUM PLANT NAMED 94-4

[75] Inventor: Richard J. Henny, Tavares, Fla.

[73] Assignee: Florida Foundation Seed Producers, Inc., Greenwood, Fla.

[21] Appl. No.: 103,572

[22] Filed: Aug. 9, 1993

[51] Int. Cl.[5] ..... A01H 5/00

[52] U.S. Cl. ..... Plt./88.1

[58] Field of Search ..... Plt. 88.1

*Primary Examiner*—James R. Feyrer

*Attorney, Agent, or Firm*—Foley & Lardner

[57] ABSTRACT

An Anthurium plant named 94-4 having red spathes with a red-purple spadix, red-brown pedicels, leaf veins, midribs, and petioles; compact, branched habit, and dark green shiny leaves.

1 Drawing Sheet

1

The present invention comprises a new and distinct cultivar of Anthurium, botanically known as *Anthurium hybrid,* and referred to by the cultivar name 94-4.

The new cultivar is a product of a planned breeding program carried out by the inventor Richard J. Henny in Apopka, Fla. The seedling is a result of the crosses set out in Table 1 which follows:

| |
|---|
| Anth. antioquense X unidentified Anth. andraenum ('G-79') = Anth. '1-1' |
| Anth. antioquense X Anth. '1-1' = Anth. '4-1' |
| Anth. amnicola X Anth. 'G-79' = Anth. '3-1' |
| Anth. '3-1' X Anth. '4-1' = Anth. '7-2' |
| Anth. '7-2' X Anth. 'Lady Jane' = Anth. '94-4' |

The cultivar was discovered in Apopka, Fla. from the progeny of the stated cross by the inventor Richard J. Henny. Propagation by division by the inventor in Apopka, Fla. increased the number of plants for evaluation and has demonstrated the stability of the combination of characteristics of the new cultivar from generation to generation.

The following observations, measurements and values describe plants grown in Apopka, Fla. under greenhouse conditions which approximate those generally used in horticultural practice.

The following traits have been repeatedly observed to the characteristics which in combination distinguish the new cultivar from other Anthuriums of the same general type, for example, the well known cultivar Lady Jane.

1. The plant produces attractive red spathes, with a red-purple spadix, carried on dark red-brown pedicels.
2. The flowers are held among and above the foliage.
3. The leaves are dark green, shiny and often have red-brown mid-ribs and veins.
4. The plant habit is compact and upright.
5. The plant is free branching.

Color references are to The Royal Horticultural Society Colour Chart. Colors may vary somewhat depending on horticultural practices such as light level and fertilization rate, among others, without, however, any variance in genotype.

The color photographic drawing comprises a top perspective view of the inflorescence and foliage of 94-4. The photograph is of a plant of 94-4 in a 15.3 cm pot approximately 16 months after planting a small 4-5 leaf cutting obtained by division and grown under appropriate growing conditions. Colors are as accurate as possible with color illustrations of this type.

2

Origin: Seedling parentage set forth in Table 1.

Classification: Anthurium hybrid cv. 94-4.

Propagation: Asexual production either by tissue culture or division.

Plant: In a 15.3 cm pot for a plant grown from a small 4-5 leaf cutting after 16 months under appropriate growing conditions, 94-4 will reach a mature size of approximately 36 cm to 38 cm in height and approximately 42 cm to 45 cm in width.

Leaves:

*Form.*—The leaf blade is ovate with a acuminate tip and an obtuse base. The margins are entire. The midrib tends to curve slightly downward toward the tip of the leaf. The leaf blade tends to be somewhat wavy over the width of the leaf.

*Size.*—Leaf blades of a mature sized plant are approximately 20.6 cm to 21 cm in length and approximately 8.8 cm to 9.1 cm in width.

*Petiole.*—The petiole is approximately 19.3 cm to 20.4 cm in height from the base of the petiole to the base of the leaf blade on the primary shoot. Secondary shoots are somewhat smaller depending on the age of the shoot. The petiole is approximately 3.0 mm to 3.5 mm in diameter just below the geniculum, and below the geniculum the petiole is straight.

*Petiole wings.*—Petiole wings are approximately 1.5 cm to 1.7 cm in length and approximately 2.5 cm to 3.0 m in width at their midpoint. The tip of the petiole wings is acute. There is approximately 18.1 to 18.4 cm between the top of the wing and the base of the geniculum.

*Geniculum.*—The geniculum is approximately 27 mm to 34 mm in length, approximately 4 mm to 4.5 mm in diameter, and is straight or slightly curved. The color is 200 C-D on the upper surface which is exposed to direct light. The lower surface is 152-A. There is no space between the top of the geniculum and the base of the leaf blade. The geniculum is prominent.

*Veins.*—Veins are sunken, with the leaf blade slightly convex between veins on the upper surface. The midrib protrudes from the upper surface of the leaf for approxixmately ⅔ the length of the leaf. Well defined primary veins on leaves radiate out from the juncture of the petiole and the leaf. Veins stand out prominently on the lower side. There are approximately 6 primary veins on each leaf.

*Lobes.*—The leaf has two lobes extending past the petiole. The distance from the petiole/leaf juncture to the highest point on the lobes is approximately 5.0 cm to 6.0 cm.

*Color.*—Upper surface: Darker than 139A. Lower surface: 147B. Midrib, upper surface: greener than 200 C-D. Midrib, lower surface: 152A. Petiole: Upper surface when exposed to direct light is greener than 200 C-D; lower surface 152A. Petiole wing: 145A.

Inflorescence:

*Immature spathe.*—The spathe is tightly rolled around the spadix and extrudes from the petiole sheath. The spathe is substantially fully open when the pedicel is fully elongated, approximately 21.9 cm to 25 cm above the soil surface. The color of the pedicel is greener than 183A.

*Mature spathe.*—Size: The flattened spathe is approximately 5.5 cm to 6.3 cm long and approximately 3 cm to 3.5 cm in width. Color, fully open: Upper surface: 53B. Lower surfaec: 53C. Color, faded: Upper surface: 51B. Lower surface: 50C. Arrangement: The spathe stands up on straight wiry pedicels and opens vertically above the leaves. Shape: The spathe is ovate with an obtuse or slightly cordate base and a cuspidate apex that is curved. It is slightly cupped when first open, approximately 5 cm to 6.2 cm in height, approximately 2.9 cn to 3.4 cm in width, and approximately 5 mm to 8 mm in depth. The spathe flattens and may develop somewhat wavy margins as it ages. Flowering time: After approximately 15–18 months from a small 4–5 leaf cutting for an untreated plant as illustrated and depending on season, approximately 2 to 4 blossoms are present. Smaller blossoms may occur on less mature growth.

Reproductive organs:

*Spadix.*—Size: Approximately 3.3 cm to 4.0 cm in height and approximately 5 mm to 6 mm in width. Color: When the spathe unrolls, the spadix is 79A at the tip, blending to 79C. The spadix gradually changes to 75B-C before senescing. Stamens: Anthers and filaments are not clearly visible. Pollen: 158C. Pistil: The pistil is crystalline appearing, 155D in color, and protrudes between the staminate flowers. They are firmly fixed to the main axil. The pistilate flowers extend approximately 0.5 mm beyond the staminate flowers.

*Roots.*—White fleshy roots with fine laterals. Roots initiated above the soil have a light pink (48B) cast.

GENERAL OBSERVATIONS

Anthurium 94-4 produces attractive red spathes with a contrasting red-purple spadix carried on dark red-brown pedicels. The plant is free flowering, with flowers held among and above the foliage. The plant habit is branched, upright and compact. The leaves are dark green and shiny; the veins, midribs and petioles are often red-brown in color.

I claim:

1. A new and distinct cultivar of Anthurium plant named 94-4, as illustrated and described.

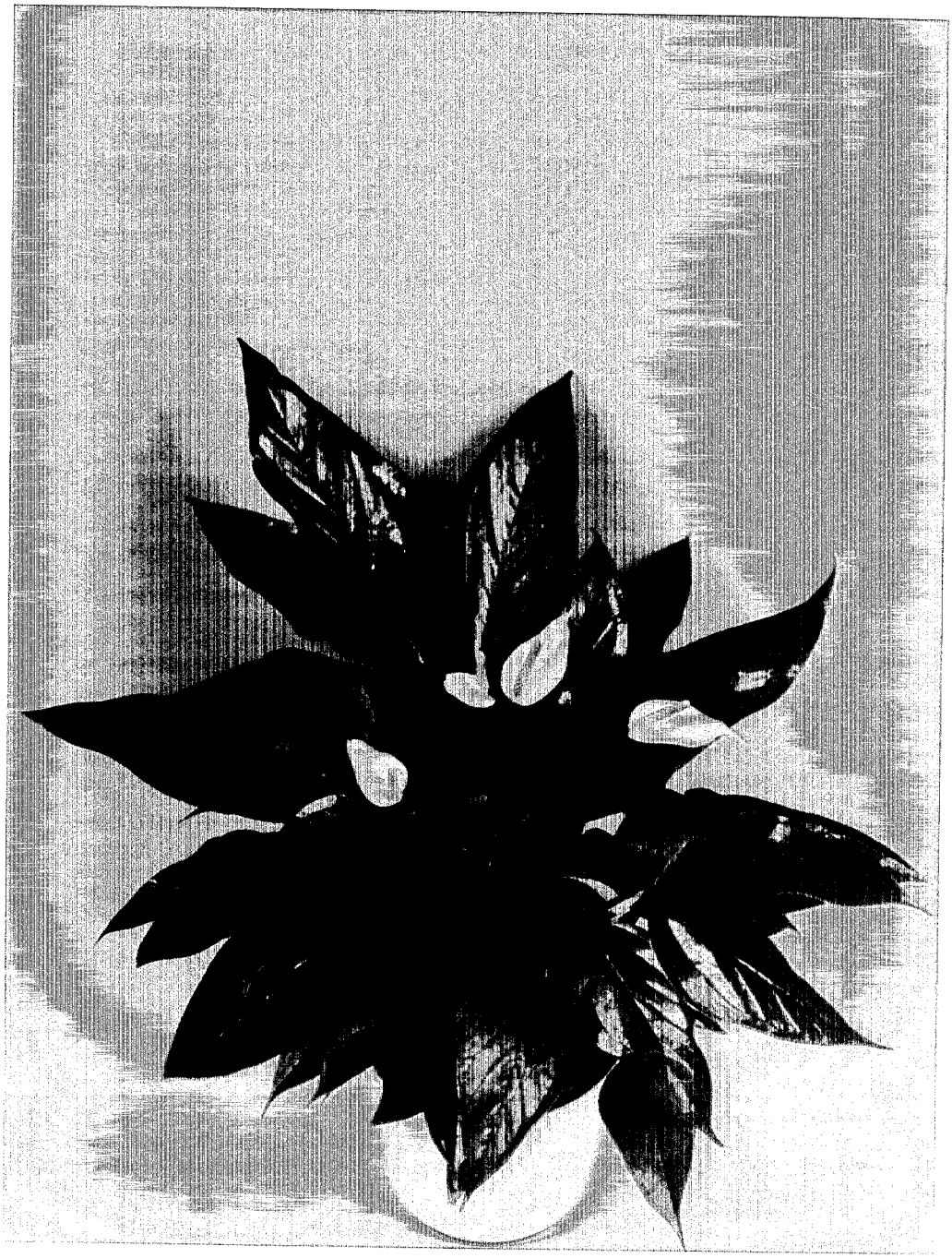

* * * * *